(12) United States Patent
Bombardelli

(10) Patent No.: US 6,500,966 B1
(45) Date of Patent: Dec. 31, 2002

(54) PROCESS FOR THE PREPARATION OF TAXANES FROM 10-DEACETYLBACCATIN III

(75) Inventor: Ezio Bombardelli, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/913,891

(22) PCT Filed: Feb. 23, 2000

(86) PCT No.: PCT/EP00/01471

§ 371 (c)(1),
(2), (4) Date: Aug. 17, 2001

(87) PCT Pub. No.: WO00/52003

PCT Pub. Date: Sep. 8, 2000

(30) Foreign Application Priority Data

Mar. 2, 1999 (IT) .......................................... MI99A0417

(51) Int. Cl.[7] ............................................ C07D 305/14
(52) U.S. Cl. ...................................................... 549/510
(58) Field of Search .......................................... 549/510

(56) References Cited

U.S. PATENT DOCUMENTS

| | | | |
|---|---|---|---|
| RE34,277 E | 6/1993 | Denis et al. ................. | 549/510 |
| 5,476,954 A | 12/1995 | Bourzat et al. .............. | 549/510 |
| 5,621,121 A | 4/1997 | Commercon et al. ........ | 549/510 |
| 5,637,723 A | 6/1997 | Commercon et al. ........ | 548/215 |
| 6,130,336 A | 10/2000 | Kim et al. ................... | 548/215 |
| 6,147,234 A | 11/2000 | Holton et al. ................ | 549/510 |

*Primary Examiner*—T. A. Solola
(74) *Attorney, Agent, or Firm*—Pennie & Edmonds LLP

(57) ABSTRACT

A process for the preparation of taxane derivatives by reacting 10-deacetylbaccatin III protected at the 7-and 1-positions with trichloroacetyl groups with a compound of formula

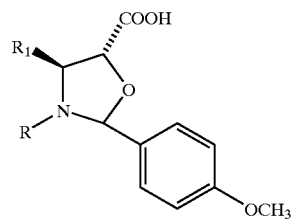

and subsequent removal of the protective groups and hydrolysis of the oxazolidine ring.

11 Claims, No Drawings

PROCESS FOR THE PREPARATION OF TAXANES FROM 10-DEACETYLBACCATIN III

This application is a 371 of PCT/EP00/01471 filed Feb. 23, 2000.

TECHNICAL FIELD

The present invention relates to a process for the preparation of taxanes from 10-deacetylbaccatin III.

The present invention relates to a process for the preparation of taxanes from 10-deacetylbaccatin III.

BACKGROUND OF THE INVENTION

Paclitaxel is a known antitumor drug with taxan structure, whose industrial preparation is particularly complex.

Paclitaxel was first isolated by extraction from the trunk barks of *Taxus brevifolia*, and it is at present synthesized starting from 10-deacetylbaccatin III, an intermediate present in the leaves of different species of taxus, particularly in those of *Taxus baccata* L., thereby overcoming the environmental problems connected with the availability of bark of *T. brevifolia*.

A number of synthetic methods are reported in literature: U.S. Pat. No. Re. 34,277 (reissue of U.S. Pat. No. 4,924,011) discloses the. semi-synthesis of Paclitaxel starting from 10-deacetylbaccatin III protected at the C-7 hydroxyl group with a trialkylsilyl group, in particular triethylsilyl, and at the 10-position with an acetyl group. In WO 98/08832, the protection of the C-7 hydroxyl group is carried out using a trichloroacetyl group. The thus protected baccatin III derivative is reacted with acetyl bromide and, subsequently, with the suitable phenylisoserine derivative to obtain Paclitaxel, following deprotection of the hydroxyl groups at 7 and 2' and benzoylation of the amine.

In WO 93/06094, Paclitaxel is prepared by reacting a beta-lactam-type compound with 7-triethylsilyl-baccatin III. The desired product is obtained by deprotection in acid medium.

In U.S. Pat. No. 5,476,954, the synthesis of Paclitaxel is carried out starting from 10-deacetylbaccatin III, protecting the C-7 hydroxyl with 2,2,2-trichloroethoxycarbonyl(Troc) and the C-10 hydroxyl with Troc or with an acetyl group.

It is therefore evident that the critical step for the synthesis of Paclitaxel is the selective esterification at C-7 with a group easily and selectively removable. Until now, 7-triethylsilyl-deacetylbaccatin III has been considered the key intermediate. The yield reported for the derivatization of 10-deacetylbaccatin III to 7-triethylsilyl-10-deacetylbaccatin III is about 85%, using 5 to 20 mols of silylating agent. The yield of the subsequent acetylation to give 7-triethylsilylbaccatin III is also about 85%.

U.S. Pat. No. 5,621,121 and U.S. Pat. No. 5,637,723 disclose the synthesis of taxanes, including Paclitaxel, by reacting suitably protected baccatin III or 10-deacetylbaccatin III with oxazolidine-5-carboxylic acids bearing at the 2-position a phenyl group substituted with alkoxy groups (U.S. Pat. No. 5,621,121) or with trihaloalkyl groups, in particular trichloromethyl (U.S. Pat. No. 5,637,723), followed by deprotection by opening of the oxazolidine ring.

The protective groups considered particularly suitable comprise silyl, 2,2,2-trichloroethoxycarbonyl or 2-(2 (trichloromethyl)propoxy)carbonyl groups.

Substantially the same methods can also be used for the preparation of Docetaxel, another known taxan derivative widely used in clinics.

It has now been found a process for the preparation of taxanes, in particular Paclitaxel and Docetaxel, which attains higher yields than the known methods.

SUMMARY OF THE INVENTION

It has now been found a process for the preparation of taxanes, in particular Paclitaxel and Docetaxel, which attains a higher yield than known methods.

The process of the invention, shown in the following Scheme, comprises:

a) simultaneous protection of the hydroxyl groups at the 7- and 10-positions of 10-deacetylbaccatin III with trichloroacetyl groups.

b) subsequent esterification of the hydroxyl at the 13-position by reaction with a compound of formula (VII):

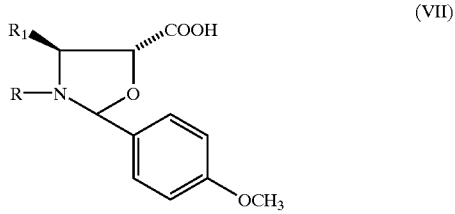

wherein R is tert.butoxycarbonyl, benzoyl or the residue of a straight or branched aliphatic acid and $R_1$ is phenyl or a straight or branched alkyl or alkenyl;

c) removal of the trichloroacetic protective groups;

d) optional selective acetylation of the hydroxyl at the 10-position, for those compounds in which $R_2$ is acetyl;

e) acid hydrolysis of the oxazolidine ring.

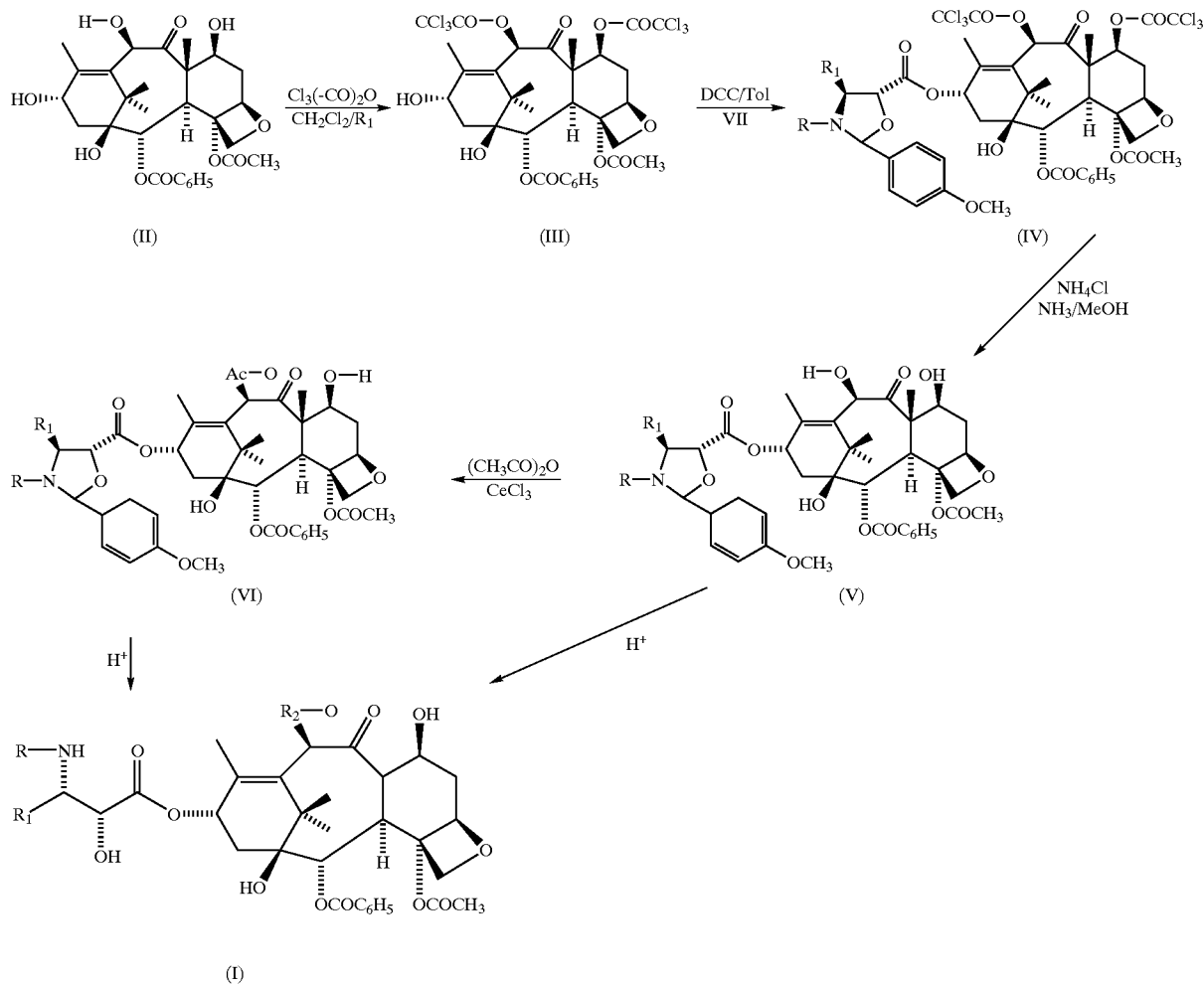

DETAILED DESCRIPTION OF THE PREFERRED EMBODIMENTS

The process of the invention differs from those of the prior art in the that the reaction sequence used provides a simpler route than those processes cited above and a remarkable improvement in the obtained yields.

The process of the invention differs from those of the prior art in that the reaction sequence used provides a simpler route than the known processes cited above and a remarkable improvement in the obtained yields.

Step a) is conventionally effected with trichloroacetic anhydride in suitable solvents and in the presence of bases such as pyridine, triethylamine and the like.

The esterification with the oxazolidine-5-carboxylic acid derivative is carried out in the presence of a condensing agent such as dicyclohexylcarbodiimide or other known reagents, in an anhydrous organic solvent, preferably aliphatic, aromatic or chlorinated hydrocarbons, at temperatures ranging from room temperature to the boiling temperature of the solvent.

The resulting oxazolidine ester is then deprotected by removing the 7- and 10-trichloroacetyl groups by treatment with $NH_4OH/NH_4Cl$ in aliphatic alcohols, preferably methanol.

The selective acetylation of the hydroxyl at the 10-position is carried out with acetic anhydride in the presence of cerium III, scandium or ytterbium salts, in a solvent such as tetrahydrofuran, dichloromethane, ethyl acetate, at temperatures ranging from 5 to 40° C.

The treatment with organic or inorganic acids in solvents such as methanol, ethanol, tetrahydrofuran, at temperatures ranging from about −2 to +2° C., yields the desired taxane derivatives. The use of formic acid in tetrahydrofuran at a temperature of 0° C. is particularly preferred.

The oxazolidine intermediates are known or can be prepared with known methods, by reaction of an isoserine ester with 4-methoxy-benzaldehyde.

The choice of anisic aldehyde proved to be particularly important for the formation of the oxazolidine, in that oxazolidine acid, contrary to the methods described in U.S. Pat. Nos. 5,621,121, 5,637,723 (Rhône-Poulenc Rorer), and in U.S. Pat. No. 5,821,363 (UpJohn), can easily be crystallized and adjusted to a 95:5 isomer ratio, which is extremely useful and advantageous for the subsequent step. Furthermore, the oxazolidine carboxylic acid obtainable with anisic aldehyde is particularly stable during the deprotection of the trichloroacetic ester and the subsequent acetylation step. In these conditions, 2,4-dimethoxybenzaldehyde used in U.S. Pat. No. 5,821,363 or chloral or p-trichloromethyl-benzaldehyde as described in U.S. Pat. Nos. 5,621,121 and 5,637,723 (Rhône-Poulenc Rorer) are not sufficiently stable.

The process of the invention, in addition to Paclitaxel (R=benzoyl, $R_1$=phenyl) and Docetaxel (R=tert.butoxycarbonyl, $R_1$=phenyl), also provides other taxane derivatives efficiently and conveniently.

The compounds of formula IV have never been described before and are therefore a further object of the invention, as intermediates useful for the synthesis of taxane derivatives.

The following Examples illustrate the invention in greater detail.

EXAMPLE 1

Preparation of 7,10-bis-trichloroacetyl-10-deacetylbaccatin III

A solution of 10 g of 10-deacetylbaccatin III (18.4 mmol) in 125 ml of dry methylene chloride and 42 ml of pyridine is added dropwise with 4.77 ml of trichloroacetic anhydride (42.32 mmol). The reaction mixture is stirred for three hours or anyhow until completion of the reaction, checked by TLC on silica gel using a 5:5 n-hexane/ethyl acetate mixture as eluent. Upon completion of the reaction, 5 ml of methanol are added to destroy the trichloroacetic anhydride excess, then water. The organic phase is thoroughly washed with HCl (0.1 M solution in water) to remove pyridine, whereas the remaining organic phase is dried over $MgSO_4$ and concentrated to dryness under vacuum. A pale yellow solid (17 g) is obtained, which upon crystallization from chloroform shows the following chemical and spectroscopical characteristics:

IR (KBr) 3517, 1771, 1728, 1240, 981, 819, 787, 675 $cm^{-1}$;

$^1$H-NMR (200 MHz); δ8.11 (Bz AA'), 7.58 (Bz C), 7.46 (Bz, BB'), 6.50 (s, H-10), 5.72 (m, H-H-2), 5.02 (d, J=8 Hz, H-5), 4.95 (m, H-13), 4.37 (d, J=8 Hz, H-20a), 4.18 (d, J=8 Hz, H-20b), 4.02 (d, J=6 Hz, H-3), 2.32 (s, 4-Ac), 2.22 (s, H-18), 1.91 (s, H-19), 1.25 and 1.11 (s, H-16, H-17), m.p.=172–175° C., $[\alpha]_D$–36° (MeOH; C=0.6).

EXAMPLE 2

Preparation of 13-(2-(4-methoxyphenyl)-N-benzoyl-4-phenyl-oxazolidyl-)-10-deacetylbaccatin III 17 g of 7,10-bistrichloroacetyl-10-deacetylbaccatin III are dissolved in 250 ml of anhydrous toluene and added under stirring with 12.6 g of 2-(4-methoxyphenyl)-N-benzoyl-4-phenyl-oxazolidine-5-carboxylic acid and 6 g of DCC. After stirring overnight at 40° C., the reaction mixture is filtered and concentrated to dryness. The residue is dissolved in 300 ml of methanol/tetrahydrofuran and added with 24 ml of a 2M $NH_3$ aqueous solution. After 1.5 hours at room temperature the reaction mixture is concentrated to small volume under vacuum, then diluted with water and the whole is extracted with ethyl acetate. The extract is concentrated to dryness and the residue is purified on a silica gel column, eluting the product with a 1:1 ethyl acetate/petroleum ether mixture, to obtain 16.8 g of the title product with m.p. 135° C. and $[\alpha]_D$=–58° (MeOH, C=0.5).

EXAMPLE 3

Preparation of 13-(2-(4-methoxyphenyl)-N-benzoyl-4-phenyl-oxazolidyl)-baccatin III A solution of 13.7 g of the product of example II in 200 ml of tetrahydrofuran is added with 56 ml of a 10% suspension of $CeCl_3.7H_2O$ in tetrahydrofuran, followed by 5.5 ml of acetic anhydride. After stirring overnight at room temperature, the reaction mixture is filtered, the filtrate is treated with methanol and concentrated to small volume; the mixture is diluted with $H_2O$ and the product is extracted with ethyl acetate, to obtain 12 g (84%) of 13-(2-(4-methoxybenzilydene)-N-benzoyl-4-phenyl-oxazolidyl-)-baccatin III having the following physical and spectroscopical characteristics:

$^1$-NMR: 8.07 (d, Bz) 7.60–7.19 (m, aromatic), 7.48–6.90 (AA', BB', p-OMePh), 6.33 (s, H-10), 5.67 (d, J=5 Hz, H-2), 5.56 (br s, H-3'), 4.93 (d, J=8 Hz, H-5), 4.90 (brs, H-2'), 4.45 (m, H-7), 4.28 (d, J=8 Hz, H-20a), 4.16 (d, J=8 Hz, H-20b), 3.82 (s, OMe), 2.27 (s, Ac), 2.08 (s, OAc), 1.66 (s, H-19), 1.29–1.16 (s, H-16, H-17), m.p. 146° C., $[\alpha]_D$=–62° (MeOH, C=0.8).

EXAMPLE 4

Preparation of Paclitaxel 12 g of 13-(2-(4-methoxyphenyl)-N-benzoyl-4-phenyl-oxazolidyl)-baccatine III are dissolved in 50 ml of tetrahydrofuran and added at 0° C. with 5 ml of formic acid; the reaction mixture is left under stirring at 0° C. for three hours, then diluted with water; formic acid is neutralized with $KHCO_3$ and the suspension is repeatedly extracted with ethyl acetate. The ether-acetic extracts are washed with water and concentrated to small volume. Upon crystallization from the same solvent, 10.5 g of Paclitaxel are obtained having the same chemical-physical and spectroscopical characteristics as described in literature.

EXAMPLE 5

Preparation of Docetaxel 17 g of 7,10-bistrichloroacetyl-10-deacetylbaccatin III are dissolved in 250 ml of anhydrous toluene and added under stirring with 11.6 g of 2-(4-methoxyphenyl)-N-tert.butoxycarbonyl-4-phenyl-oxazolidine-5-carboxylic acid and 6 g of DCC. After stirring overnight at 40° C., the reaction mixture is filtered and concentrated to dryness. The residue is dissolved in 300 ml of methanol/tetrahydrofuran and added with 24 ml of a 2M $NH_3$ aqueous solution. After 1.5 hours at room temperature, the reaction mixture is concentrated to small volume under vacuum, then diluted with water and the whole is extracted with ethyl acetate. The extract is concentrated to dryness and 10 g of this residue are dissolved in THF and added at 0° C. with 5 ml of formic acid. The reaction mixture is left under stirring at 0° C. for three hours, then diluted with water; formic acid is neutralized with $KHCO_3$, the suspension is repeatedly with ethyl acetate. The organic extracts are washed with water and concentrated to small volume. Upon crystallization from the same solvent, 9.2 g of Docetaxel are obtained having the same chemical, physical and spectroscopical characteristics as described in literature.

What is claimed is:

1. A compound of Formula (IV)

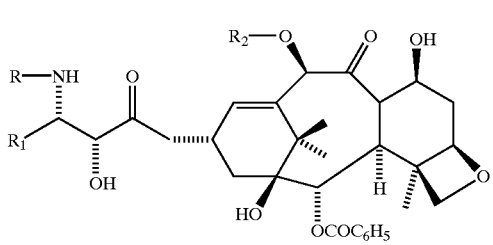

(IV)

wherein R is a tert-butoxycarbonyl, benzoyl, or straight or branched chain alkyl carbonyl group; $R_1$ is a phenyl or a straight or branched alkyl or alkenyl group; and $R_2$ is hydrogen or an acetyl group.

2. A process for preparing a compound of formula I

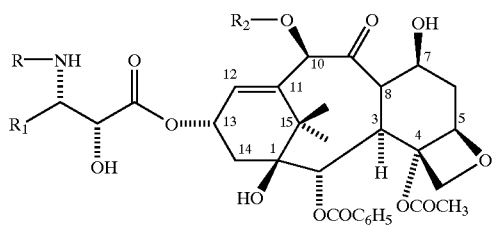

(I)

wherein R is a tert-butoxycarbonyl, benzoyl, or straight or branched chain alkyl carbonyl group; $R_1$ is a phenyl or a straight or branched alkyl or alkenyl group; and $R_2$ is hydrogen or an acetyl group comprising (a) simultaneously protecting the C-7 and C-10 hydroxyl groups of 10-deacetylbaccatin III with trichloroacetyl groups to provide a protected 10-deacetylbaccatin III, (b) esterifying the C-13 hydroxyl group of the protected 10-deacetylbaccatin III with an oxazolidine 5-carboxylic acid of formula II

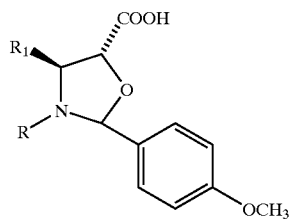

wherein R is a tert-butoxycarbonyl, benzoyl, or straight or branched chain alkyl carbonyl group; $R_1$ is a phenyl or a straight or branched alkyl or alkenyl group to provide a protected C-13 esterified 10-deacetylbaccatin III having an oxazolidine ring at the C-13 position;

(c) removing the trichloroacetyl groups from the protected C-13 esterified 10-deacetylbaccatin III to provide a C-13 esterified 10-deacetylbaccatin III;

(d) optionally acetylating the C-10 hydroxyl group of the C-13 esterified 10-deacetylbaccatin III; and (e) hydrolyzing the oxazlodine ring of the protected C-13 esterified 10-deacetylbaccatin III in the presence of an acid.

3. The process of claim 2, wherein step (b) is carried out in the presence of a condensing agent and a base.

4. The process of claim 3, wherein the condensing agent is dicyclohexylcarbodiimide.

5. The process of claim 4, wherein the base is pyridine.

6. The process of claim 2, wherein step (c) is carried out using $NH_4OH/NH_4Cl$ in an aliphatic solvent.

7. The process of claim 2, wherein step (d) is carried out by reacting the C-13 esterified 10-deacetylbaccatin III with acetic anhydride in the presence of a cerium III, scandium, or ytterbium salt.

8. The process of claim 2, wherein step (e) is carried out by reacting the protected C-13 esterified 10-deacetylbaccatin III with an organic acid or an inorganic acid in an aliphatic alcohol or tetrahydrofuran.

9. The process of claim 8, wherein the acid is formic acid.

10. The process of claim 2, wherein R is a benzoyl group, $R_1$ is a phenyl group, and $R_2$ is an acetyl group.

11. The process of claim 2, wherein R is tert-butoxycarbonyl group, $R_1$ is a phenyl group, and $R_2$ is a hydrogen.

* * * * *

UNITED STATES PATENT AND TRADEMARK OFFICE
CERTIFICATE OF CORRECTION

PATENT NO. : 6,500,966 B1
DATED : August 17, 2001
INVENTOR(S) : Ezio Bombardelli It is certified that error appears in the above-identified patent and that said Letters Patent is hereby corrected as shown below:

Column 8,
Line 20, insert -- to provide a C-13 esterified baccatin III -- after the phrase "C-13 esterified 10-deacetylbaccatin III".
Line 22, insert -- or the C-13 esterified baccatin III -- after the phrase "C-13 esterified 10-baccatin III".
Line 23, insert -- to provide the compound of formula I -- after the phrase "acid".
Line 36, insert -- or the C-13 esterified baccatin III -- after the phrase "C-13 esterified 10-deactylbaccatin III".

Signed and Sealed this

Sixteenth Day of September, 2003

JAMES E. ROGAN
*Director of the United States Patent and Trademark Office*